US012584859B2

(12) United States Patent (10) Patent No.: US 12,584,859 B2
Lorsakul et al. (45) Date of Patent: Mar. 24, 2026

(54) IDENTIFYING AUTO-FLUORESCENT ARTIFACTS IN A MULTIPLEXED IMMUNOFLUORESCENT IMAGE

(71) Applicant: Ventana Medical Systems, Inc., Tucson, AZ (US)

(72) Inventors: Auranuch Lorsakul, Santa Clara, CA (US); Trung Kien Nguyen, Seattle, WA (US); Yao Nie, Sunnyvale, CA (US); Smadar Shiffman, Palo Alto, CA (US); Xingwei Wang, Sunnyvale, CA (US); Zuo Zhao, Mountain View, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 189 days.

(21) Appl. No.: 18/299,549

(22) Filed: Apr. 12, 2023

(65) Prior Publication Data

US 2023/0251199 A1     Aug. 10, 2023

Related U.S. Application Data

(63) Continuation of application No. PCT/US2021/053934, filed on Oct. 7, 2021.
(Continued)

(51) Int. Cl.
G01N 21/64 (2006.01)
G06T 5/50 (2006.01)
(Continued)

(52) U.S. Cl.
CPC ........... G01N 21/6456 (2013.01); G06T 5/50 (2013.01); G06T 5/60 (2024.01); G06T 7/0012 (2013.01);
(Continued)

(58) Field of Classification Search
CPC ..................... G06T 5/50; G06T 7/0012; G06T 2207/20221; G06T 2207/30024;
(Continued)

(56) References Cited

U.S. PATENT DOCUMENTS 11,250,568 B2 * 2/2022 Svekolkin ............... G06T 7/174
11,307,142 B2 * 4/2022 Miller ................ G01N 21/6486
(Continued)

FOREIGN PATENT DOCUMENTS

CN     111699510 A     9/2020

OTHER PUBLICATIONS

JP Application No. 2023-525046 , "Office Action", Dec. 25, 2023, 13 pages.
(Continued)

*Primary Examiner* — Daniel G Mariam
(74) *Attorney, Agent, or Firm* — Kilpatrick Townsend & Stockton LLP

(57) ABSTRACT

Embodiments disclosed herein generally relate to identifying auto-fluorescent artifacts in a multiplexed immunofluorescent image. Particularly, aspects of the present disclosure are directed to accessing a multiplexed immunofluorescent image of a slice of specimen, wherein the multiplexed immunofluorescent image comprises one or more auto-fluorescent artifacts, processing the multiplexed immunofluorescent image using a machine-learning model, wherein an output of the processing corresponds to a prediction that the multiplexed immunofluorescent image includes one or more auto-fluorescent artifacts at one or more particular portions of the multiplexed immunofluorescent image, adjusting subsequent image processing based on the prediction, performing the subsequent image processing, and out-
(Continued)

putting a result of the subsequent image processing, wherein the result corresponds to a predicted characterization of the specimen.

20 Claims, 11 Drawing Sheets
(6 of 11 Drawing Sheet(s) Filed in Color)

Related U.S. Application Data

(60) Provisional application No. 63/106,114, filed on Oct. 27, 2020.

(51) Int. Cl.

| | |
|---|---|
| *G06T 5/60* | (2024.01) |
| *G06T 7/00* | (2017.01) |
| *G06V 10/44* | (2022.01) |
| *G06V 10/70* | (2022.01) |
| *G16H 30/20* | (2018.01) |
| *G16H 30/40* | (2018.01) |

(52) U.S. Cl.
CPC .............. *G06V 10/44* (2022.01); *G06V 10/70* (2022.01); *G16H 30/20* (2018.01); *G16H 30/40* (2018.01); *G06T 2207/20221* (2013.01); *G06T 2207/30024* (2013.01); *G06T 2207/30096* (2013.01)

(58) Field of Classification Search
CPC ...... G06T 2207/30096; G01N 21/6456; G16H 30/20; G16H 30/40
See application file for complete search history.

(56) References Cited

U.S. PATENT DOCUMENTS

| | | | |
|---|---|---|---|
| 2010/0184093 A1 | 7/2010 | Donovan et al. | |
| 2012/0010528 A1 | 1/2012 | Donovan et al. | |
| 2019/0339203 A1* | 11/2019 | Miller | ................... G01J 3/2823 |

OTHER PUBLICATIONS

International Application No. PCT/US2021/053934 , "International Preliminary Report on Patentability", May 11, 2023, 10 pages.

Agerskov , "Adaptable Semi-Automated 3D Segmentation Using Deep Learning with Spatial Slice Propagation", Available Online at URL: http://www.diva-portal.org/smash/get/diva2:1282070/FULLTEXT01.pdf, Jan. 1, 2019, 39 pages.

Baharlou et al., "Digital Removal of Autofluorescence From Microscopy Images", Available Online at URL: https://www.biorxiv.org/content/10.1101/566315V1.full.pdf, Mar. 3, 2019, 25 pages.

McRae et al., "Robust Blind Spectral Unmixing for Fluorescence Microscopy Using Unsupervised Learning", Available Online at URL: https://www.biorxiv.org/content/10.1101/797993V1.full.pdf, Oct. 9, 2019, 40 pages.

International Application No. PCT/US2021/053934 , "International Search Report and Written Opinion", Jan. 25, 2022, 14 pages.

Ronneberger et al., "U-Net: Convolutional Networks for Biomedical Image Segmentation", International Conference on Medical Image Computing and Computer-Assisted Intervention, Available Online at URL: https://arxiv.org/pdf/1505.04597.pdf, May 18, 2015, pp. 234-241.

Srinivasa et al., "Active Mask Segmentation for the Cell-Volume Computation and Golgi-Body Segmentation of Hela Cell Images", 5th IEEE International Symposium on Biomedical Imaging: From Nano to Macro, May 2008, pp. 348-351.

Stack et al., "Multiplexed Immunohistochemistry, Imaging, and Quantitation: A Review, With an Assessment of Tyramide Signal Amplification, Multispectral Imaging and Multiplex Analysis", Methods, vol. 70, No. 1, Nov. 1, 2014, pp. 46-58.

Wang et al., "Red Blood Cell Artifacts Identification in Multiplexed Immunofluorescence Image Using Deep Learning", Available Online at URL: https://digitalpathologyassociation.org/_data/media/371/10082020-023424.pdf, Oct. 11, 2020, 1 page.

JP Application No. 2023-525046 , "Notice of Allowance", Apr. 18, 2024, 6 pages.

Chinese Application No. 202180073269.0, Office Action, Mailed on Jun. 27, 2025, 17 pages.

EP Application No. 21801759.8, "Office Action", Oct. 24, 2025, 11 pages.

Ronneberger et al., "U-Net: Convolutional Networks for Biomedical Image Segmentation", 18th International Conference, Munich, Germany, Oct. 5-9, 2015, Proceedings, Part III, May 18, 2015.

Wang et al., "Red Blood Cell Artifacts Identification in Multiplexed Immunofluorescence Image using Deep Learning", Through the Prism of Innovation—Oral and Poster Abstracts, Sep. 24, 2021, pp. S32-S33.

* cited by examiner

FAT Artifacts

900

905

Access a multiplexed immunofluorescent image of a slice of specimen

910

Process the multiplexed immunofluorescent image using a machine-learning model

915

Adjust subsequent image processing based on the prediction

920

Perform the subsequent image processing

925

Output a result of the subsequent image processing

IDENTIFYING AUTO-FLUORESCENT ARTIFACTS IN A MULTIPLEXED IMMUNOFLUORESCENT IMAGE

CROSS-REFERENCE TO RELATED APPLICATION

This application is a continuation of International Application No. PCT/US2021/053934, filed on Oct. 7, 2021, which claims the benefit of and the priority to U.S. Provisional Application No. 63/106,114, filed on Oct. 27, 2020. Each of these applications is hereby incorporated by reference in its entirety for all purposes.

FIELD

Methods and systems disclosed herein relate generally to processing digital pathology images. Specifically, machine learning and image processing techniques are used for identifying auto-fluorescent artifacts in multiplexed immunofluorescent images.

BACKGROUND

Digital pathology involves scanning slides of samples (e.g., tissue samples, blood samples, urine samples, etc.) into digital images. The sample can be stained such that select proteins (antigens) in cells are differentially visually marked relative to the rest of the sample. The target protein in the specimen may be referred to as a biomarker. Digital images with multiple stains for different biomarkers can be generated for a tissue sample. These digital images may be referred to as multiplexed immunofluorescent images. For example, multiplexed immunofluorescent images can allow visualization of the spatial relationship between tumorous and non-tumorous cells in a tissue sample. Image analysis may be performed to identify and quantify the biomarkers in the tissue sample. The image analysis can be performed by computing systems or pathologists to facilitate characterization of the biomarkers (e.g., in terms of presence, size, shape and/or location) so as to inform (for example) diagnosis of a disease, determination of a treatment plan, or assessment of a response to a therapy.

However, select complications pertaining to multiplexed immunofluorescent images are that light signals from different stained sample portions may interfere with each other in a manner such that detecting a single dye may be difficult and thus lead to detection inaccuracies. Further or alternatively, a given type of biological material may naturally auto-fluoresce at a given frequency. A probability that such auto-fluorescence may confuse and/or obscure interpretations of an image of a stained sample can increase when the sample is stained with multiple stains.

SUMMARY

In some embodiments, a computer-implemented method is provided. A multiplexed immunofluorescent image of a slice of specimen is accessed. The multiplexed immunofluorescent image can include one or more auto-fluorescent artifacts (e.g., auto-fluorescing biological elements, such as red blood cells, fat, tissue, or connected tissue). The multiplexed immunofluorescent image is processed using a machine-learning model (U-Net model). An output of the processing can correspond to a prediction as to whether the multiplexed immunofluorescent image includes one or more auto-fluorescent artifacts. The prediction may identify one or more particular portions of the multiplexed immunofluorescent image predicted to depict an auto-fluorescent artifact. Subsequent image processing is adjusted based on the prediction. The subsequent image processing is performed and a result of the subsequent image processing is output. The result can correspond to a predicted characterization of the specimen.

In some embodiments, the computer-implemented method can include generating a modified version of the multiplexed immunofluorescent image based on the prediction of each of the one or more auto-fluorescent artifacts. For example, the multiplexed immunofluorescent image may be modified such that each of the particular portion(s) predicted to depict an auto-fluorescent artifact is assigned a null value, a zero value, a statistical value (e.g., a median or mean) calculated based on a remainder of the multiplexed immunofluorescent image, a statistical value (e.g., a median or mean) calculated based on pixels surrounding the one or more particular portions, and/or a statistical value (e.g., a median or mean) calculated based on one or more other images. As another example, the multiplexed immunofluorescent image may be cropped to exclude the one or more particular portions. The subsequent image processing can include processing the modified version of the multiplexed immunofluorescent image.

In some embodiments, adjusting the subsequent image processing can include determining, for each of one or more regions of the image, that at least one metric corresponding to the one or more particular portions of the multiplexed immunofluorescent image exceeds a predefined threshold. For example, the metric(s) can include a cumulative size of an auto-fluorescent artifact, a total number of auto-fluorescent artifacts in the multiplexed immunofluorescent image, or a probability that the multiplexed immunofluorescent image includes at least one auto-fluorescent artifacts. The metric(s) can include at least part of the output or be generated based on the output of the processing.

In some instances, performing the subsequent image processing includes modifying each of one or more other images based on locations of the one or more particular portions of the multiplexed immunofluorescent image. Each of the one or more other images can correspond to another slice of the specimen. The one or more other modified images can be processed.

In some embodiments, the computer-implemented method can include receiving a whole slide image comprising one or more patches prior to accessing the multiplexed immunofluorescent image. A patch of the one or more patches can be selected based on identifying features in the patch. For example, edge detection may be performed on the patches, where a presence of one or more edges indicates both target regions and non-target regions are present in the patch. A patch may be selected based on detecting the presence of edges. Patches in which edges are not detected may not be selected. The selected patch can correspond to the multiplexed immunofluorescent image.

In some embodiments, the computer-implemented method can further include, prior to accessing the multiplexed immunofluorescent image, applying a first stain for a first biomarker to a sample slice of the specimen and generating a first image of the sample slice with the first stain. Further, a second stain for a second biomarker can be applied to the sample slice of the specimen, and a second image can be generated of the sample slice with the second stain. The multiplexed immunofluorescent image can be generated by combining the first and second images.

In some instances, the subsequent image processing includes detecting depictions of a set of tumor cells. The result can characterize a presence of, quantity of, and/or size of the set of tumor cells.

Some embodiments of the present disclosure include a system including one or more data processors. The system can further include a non-transitory computer readable storage medium containing instructions which, when executed on the one or more data processors, cause the one or more data processors to perform part or all of one or more of the methods disclosed herein.

In some embodiments, a computer-program product is provided that is tangibly embodied in a non-transitory machine-readable storage medium. The computer-program product can include instructions configured to cause one or more data processors to perform part or all of one or more of the methods disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure is described in conjunction with the appended figures.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

The present disclosure describes techniques for automated auto-fluorescent artifact identification. More specifically, some embodiments of the present disclosure provide machine learning techniques for identifying auto-fluorescent artifacts in multiplexed immunofluorescent images to support or improve tumor detection and analysis.

Multiplexed immunofluorescent slide staining can enable multiple proteins in a tissue section to be simultaneously detected. Multiplexed immunofluorescent images may be used in the study of different types of cells in biological tissue, blood, or urine. With respect to tissue, a biopsy of the biological tissue may be collected, fixed (e.g., using a formaldehyde solution) and embedded, after which the sample may be sliced into smaller sections. Each slice can be applied to a glass slide for staining and analysis. With respect to a liquid sample (e.g., blood or urine), a drop (or multiple drops) of the sample can be placed on a base slide, and a spreader slide can be placed on top of the sample so as to smear the sample. The slide can then be dried (e.g., air dried), fixed (e.g., using methanol), and stained. During staining, primary antibodies and one or more types of secondary antibodies can be applied to the specimen to amplify immunofluorescent signals. For multiplexed immunofluorescent staining, such as with tyramide-based staining, a horseradish peroxidase (HRP) conjugated secondary antibody can bind to an unconjugated primary antibody that is specific to the protein of interest. A fluorophore-conjugated tyramide molecule can be a substrate for the HRP, resulting in the fluorescence. The tyramide molecule can bond with a tyrosine on or neighboring the targeted protein. The primary and secondary antibody can then be removed through heat washing or other means, leaving the tyramide bonded to the targeted protein. During imaging and analysis, the fluorescent tyramide can be detected. Additional primary and secondary antigen pairs for different target proteins can repeatedly be applied to and removed from the same slice of specimen. After each primary and secondary antigen pair are applied, the slide can be scanned to generate an image of the slide. The images can be combined after the staining process to generate the multiplexed immunofluorescent image.

Figure 1A:
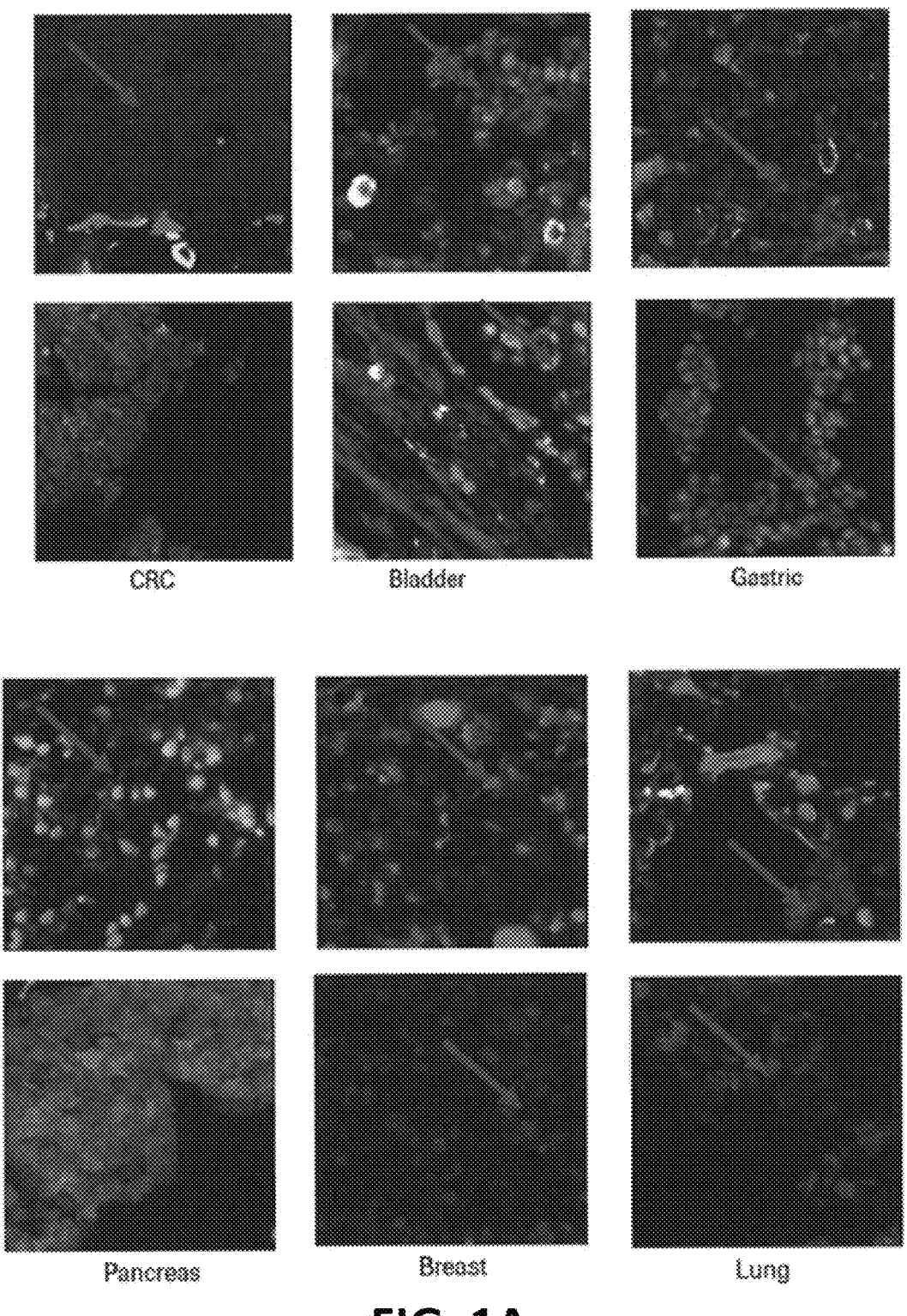
FIGS. 1A-1B show exemplary auto-fluorescent artifacts in multiplexed immunofluorescent images of different types of tissues.
Figure 1B:
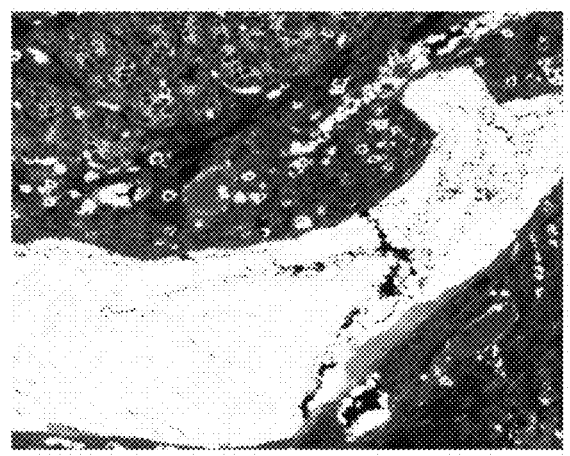
Figure 1B:
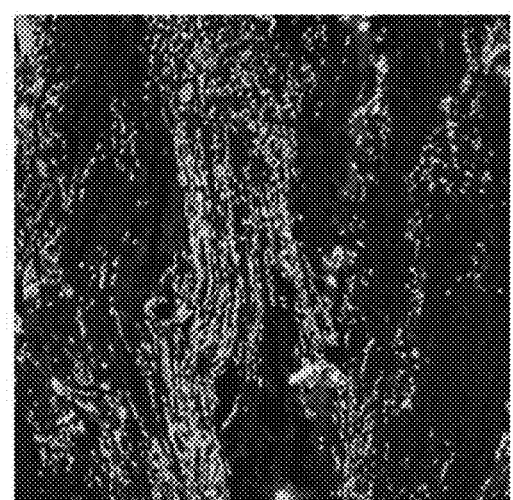
Figure 1B:
Figure 1B:
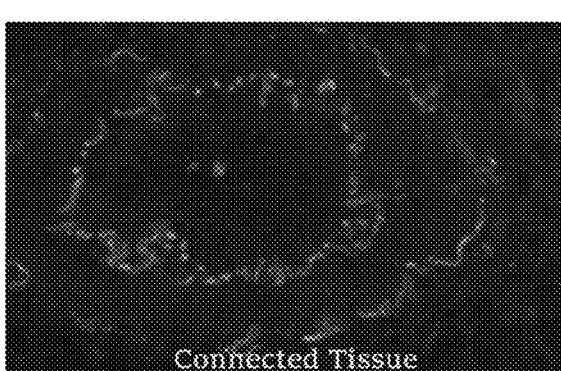
Figure 1B:
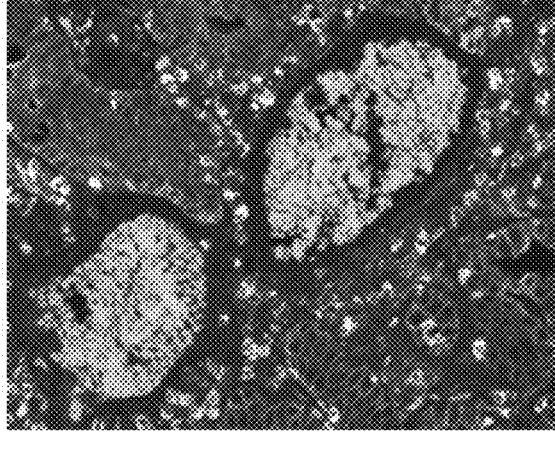

During imaging and analysis, regions of the multiplexed immunofluorescent image may be segmented into target regions (e.g., positive and negative tumor cells) and non-target regions (e.g., normal tissue or blank slide regions). Each target region can include a region of interest that may be characterized and/or quantified. In some instances, the multiplexed immunofluorescent image may include biological material or other structures that do not correspond to regions of interest that auto-fluoresce, such that it becomes difficult to differentiate target and non-target regions. For example, red blood cells, fat, tissue, or connected tissue and other auto-fluorescent materials can result in false detection of nuclei in the DAPI channel, misclassification of individual markers as positive or negative, and incorrect segmentation of tumor areas. FIGS. 1A and 1B show exemplary auto-fluorescent artifacts in multiplex immunofluorescent images. FIG. 1A includes red blood cell artifacts in multiplexed immunofluorescent images of breast, colorectal cancer, pancreas, lung, and gastric cells. FIG. 1B includes auto-fluorescent artifacts resulting from fat and connected tissue in the left column, and additional red blood cell artifacts in the right column. A pathologist may annotate areas of interest (e.g., tumor cells) in the multiplexed immunofluorescent image, while the pathologist may attempt to avoid annotating other auto-fluorescent artifact regions. These annotations may be subject to error, and can be time intensive when a large number of slides is to be processed.

Automated identification and segmentation of auto-fluorescent artifacts from multiplexed immunofluorescent images may provide more accurate and faster differentiation of auto-fluorescent artifacts and regions of interest, which can result in more efficient and better diagnosis and treatment assessment of tumors. Conventional image analysis can use intensity-based methods to identify auto-fluorescent signals in multiplexed immunofluorescent images. However, these methods have limited accuracy due to the intensity distribution of auto-fluorescent artifacts. The distribution of auto-fluorescent artifact intensities may overlap with non-artifact signals, making detection and segmentation difficult or inaccurate. As a result, conventional image analysis algorithms usually provide over-detection, under-detection, or inaccurate detection of auto-fluorescent artifacts in multiplexed immunofluorescent images.

In some embodiments, a machine-learning model is provided to predict locations of auto-fluorescent artifacts in a multiplexed immunofluorescent image. In some instances, the machine-learning model has a convolutional neural network (CNN) architecture that utilizes a U-Net model to automatically identify auto-fluorescent artifacts in multiplexed immunofluorescent images. The machine-learning model can be trained using training images that include a set of positive data elements (images containing auto-fluorescent artifacts) and a set of negative data elements (images not containing auto-fluorescent artifacts). Each positive data element may include one or more indications as to where, within the image, each artifact is depicted. Training the machine-learning model can include, for example, learning auto-fluorescent artifact characteristics or signatures (intensity and texture features). Training may also include learning adjustments for the image based on characteristics of auto-fluorescent artifacts. The trained machine-learning model can be used to predict particular portions of a multiplexed immunofluorescent image that include auto-fluorescent artifacts. In some examples, the trained machine-learning model can be used on multi-channel raw data of the multiplexed immunofluorescent image. In other examples, the trained machine-learning model may be used on a composite image generated using the multi-channel raw data. Additionally, a machine-learning model may be trained for each channel of the multi-channel raw data such that the trained machine-learning models each process a single channel (e.g., stain or signal). In some instances, the machine-learning model is performed as part of pre-processing before performing an image analysis algorithm to classify target regions within the image (e.g., tumor cells). However, as should be understood by one of ordinary skill in the art, the concepts discussed herein are not limited to pre-processing procedures, but may also be integrated into the overall image analysis processing in accordance with various embodiments.

An output can be generated that indicates the predicted particular portions of the multiplexed immunofluorescent image containing auto-fluorescent artifacts. In examples where a different machine-learning model is used for each channel, the output of each machine-learning model can be combined to create a combined prediction for the multiplexed immunofluorescent image. In some examples, the machine-learning model may adjust the multiplexed immunofluorescent image based on the prediction and learned adjustment parameters. Subsequent image processing can also be adjusted based on the output. For example, the multiplexed immunofluorescent image may be modified based on the prediction. Additionally or alternatively, modified versions of other multiplexed immunofluorescent images corresponding to another slice of the specimen may be generated based on the output. As yet another additional or alternative example, a condition may be evaluated as to whether to exclude the multiplexed immunofluorescent image from subsequent image processing based on the output. The subsequent image processing can include processing one or more multiplexed immunofluorescent images and/or modified versions thereof (e.g., processing a modified version of the multiplexed immunofluorescent image, processing one or more other multiplexed immunofluorescent images and/or processing modified versions of one or more other multiplexed immunofluorescent images) and outputting a result. The result can characterize a presence of, location of, quantity of, and/or size of a set of tumor cells in the multiplexed immunofluorescent image. The result may be used to determine a diagnosis, a treatment plan, or to assess an ongoing treatment for the tumor cells.

II. Definitions and Abbreviations

As used herein, the term "auto-fluorescent artifact" refers to biological components that naturally emit light when they absorb light. For example, red blood cells, fat, flavin, elastin, connected tissue, and collagen exhibit auto-fluorescence when they absorb light. In some embodiments, the term "auto-fluorescent artifact" refers to biological components that interfere with detection of structures targeted by fluorescent markers.

As used herein, the term "multiplexed immunofluorescent image" refers to a whole slide image or a patch of a whole slide image of a biological specimen (e.g., a tissue slice, blood smear or urine smear) that has been stained for multiple biomarkers. Each of the biomarkers can fluoresce at a different wavelength when excited, such that each biomarker can be uniquely identified.

As used herein, the term "patch" or "image patch" refers to a collection of pixels corresponding to a portion of a whole slide image. In some embodiments, "patch" or "image patch" refers to a region of a whole slide image or an area of interest having (x,y) pixel dimensions (e.g., 256 pixels by 256 pixels). For example, a whole slide image of 1000 pixels by 1000 pixels divided into 100 pixel×100 pixel patches would comprise 100 patches (each patch containing 10,000 pixels). In other embodiments, the patches overlap with each "patch" or "image patch" having (x,y) pixel dimensions and sharing one or more pixels with another "patch" or "image patch".

As used herein, the term "slice of specimen" refers to any biological sample (such as tissue sections, needle biopsies of tissue, blood, and urine) from an organism. Examples of organisms include humans, veterinary animals, and laboratory animals. In certain embodiments, the term "slice of specimen" as used herein refers to a sample prepared from a tumor or a portion thereof obtained from a subject.

III. Computing Environment and Model Architecture

Figure 2:
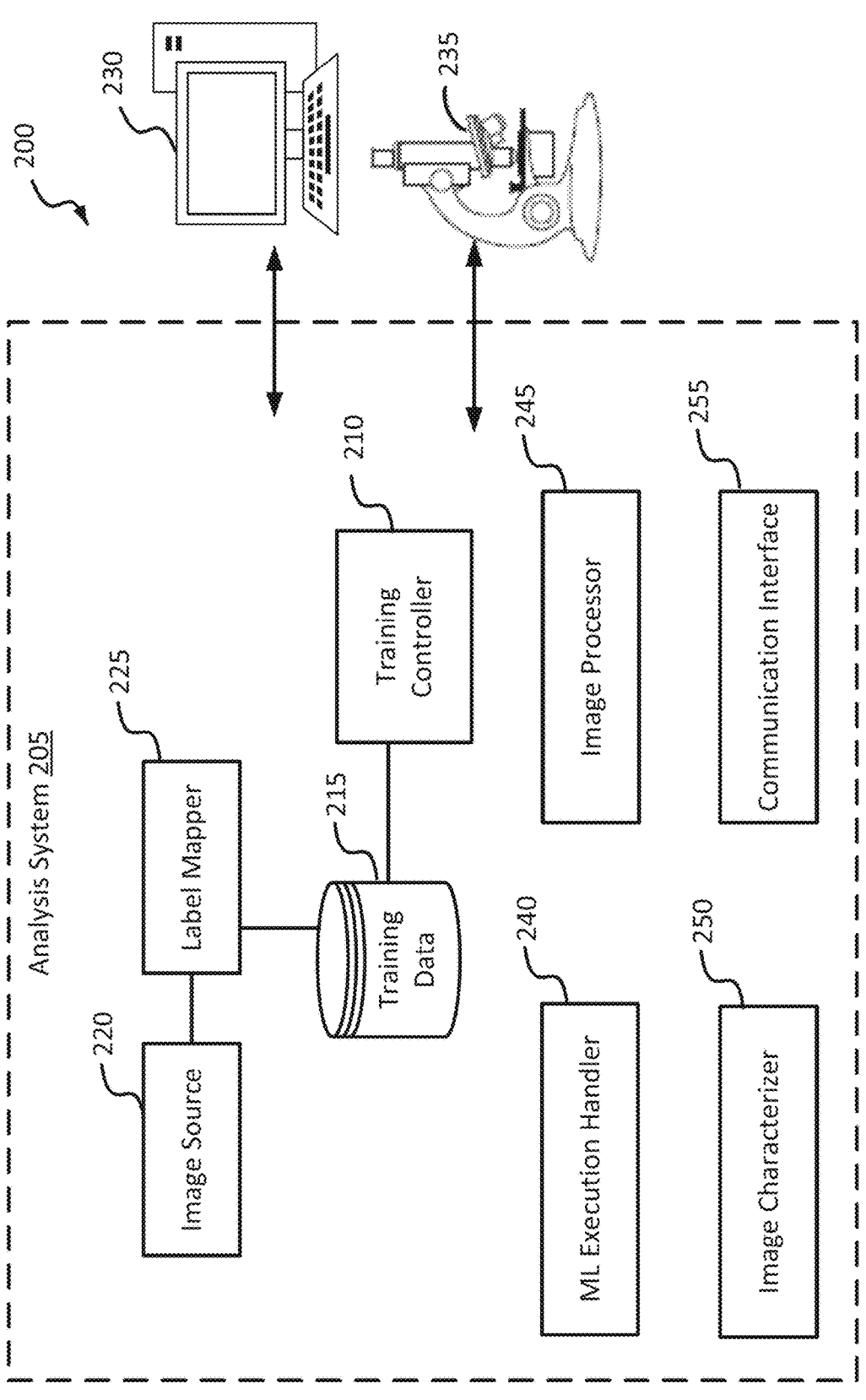
FIG. 2 shows an exemplary computing system for training and using a machine-learning model to identify results of facilitating auto-fluorescent artifact identification.

FIG. 2 shows an exemplary computing system 200 for training and using a machine-learning model to facilitate detecting auto-fluorescent artifact identification and for processing digital-pathology images. The computing system 200 can include an analysis system 205 to train and execute the machine-learning model. Examples of the machine-learning model can be a deep convolutional neural network, a U-Net, a V-Net, a residual neural network, or a recurrent neural network. The machine-learning model may be trained and/or used to (for example) predict whether a multiplexed immunofluorescent image includes one or more auto-fluorescent artifacts, such as red blood cells (RBCs), fat, tissue, or connected tissue. The analysis system 205 may further train and/or use one or more other machine-learning models to perform another type of detection (e.g., depicting tumor cells). The other machine-learning model(s) may include (for example) a convolutional neural network, a U-Net, and/or deep neural network. In some instances, an image is processed using results from the artifact-detection machine-learning model (e.g., to remove or obscure each artifact), and the other machine-learning model(s) can receive and use the processed image to perform the other type of detection. In some instances, results from the artifact-detection machine-learning model are used to identify patches and/or images that are to be excluded data used to perform the other type of detection.

A training controller 210 can execute code to train the artifact-detection machine-learning model and/or the other machine-learning model(s) using one or more training data sets 215. Each training data set 215 can include a set of training multiplexed immunofluorescent images. Each of the multiplexed immunofluorescent images may include a digital pathology image that depicts one or more biological objects (e.g., a set of cells of one or more types). Each image in a first subset of the set of training multiplexed immunofluorescent images may include one or more auto-fluorescent artifacts, and each image in a second subset of the set of training multiplexed immunofluorescent images may lack auto-fluorescent artifacts. Each of the multiplexed immunofluorescent images may depict a portion of a sample, such as a tissue sample (e.g., colorectal, bladder, breast, pancreas, lung, or gastric tissue), a blood sample or a urine sample. In some instances, each of one or more of the multiplexed immunofluorescent images depicts a plurality of tumor cells. The training data 215 may have been collected (for example) from an image source 220, such as a public data store, and/or from data received from (for example) one or more laboratories.

The computing system 200 can include a label mapper 225 that maps multiplexed immunofluorescent images from the image source 220 containing auto-fluorescent artifacts to an "auto-fluorescent artifact" label and that maps multiplexed immunofluorescent images not containing auto-fluorescent artifacts to a "non-artifact" label. The auto-fluorescent artifacts can include red blood cells, collagen, elastin, flavin, and other biological components that exhibit auto-fluorescence. Mapping data may be stored in a mapping data store (not shown). The mapping data may identify each multiplexed immunofluorescent image that is mapped to either of the auto-fluorescent artifact label or non-artifact label.

In some instances, labels associated with the training multiplexed immunofluorescent images may have been received or may be derived from data received from one or more provider systems 230, each of which may be associated with (for example) a physician, nurse, hospital, pharmacist, etc. associated with a particular subject. The received data may include (for example) one or more medical records corresponding to the particular subject. The medical records may indicate (for example) a professional's diagnosis or characterization that indicates, with respect to a time period corresponding to a time at which one or more input image elements associated with the subject were collected or a subsequent defined time period, whether the subject had a tumor and/or a stage of progression of the subject's tumor (e.g., along a standard scale and/or by identifying a metric, such total metabolic tumor volume (TMTV)). The received data may further include the pixels of the locations of tumors or tumor cells within the one or more multiplexed immunofluorescent images associated with the subject. Thus, the medical records may include or may be used to identify, with respect to each training multiplexed immunofluorescent image, one or more labels. In some instances, images or scans that are input to one or more classifier subsystems are received from the provider system 230. For example, the provider system 230 may receive images from an imaging device 235 and may then transmit the images or scans (e.g., along with a subject identifier and one or more labels) to the analysis system 205.

Training controller 210 can use the mappings of the training data 215 to train a machine-learning model. More specifically, training controller 210 can access an architecture of a model (e.g., U-Net model), define (fixed) hyperparameters for the model (which are parameters that influence the learning process, such as e.g. the learning rate, size/complexity of the model, etc.), and train the model such that a set of parameters are learned. More specifically, the set of parameters may be learned by identifying parameter values that are associated with a low or lowest loss, cost or error generated by comparing predicted outputs (obtained using given parameter values) with actual outputs. In some instances, a machine-learning model can be configured to iteratively fit new models to improve estimation accuracy of an output (e.g., that includes a metric or identifier corresponding to an estimate or likelihood as to portions of the multiplexed immunofluorescent image that include auto-fluorescent artifacts). The machine-learning model may additionally be trained using ground truth segmentation to determine a foreground/background probability for each pixel, where the foreground corresponds to auto-fluorescent artifacts. The machine-learning model may additionally be trained to adjust the multiplexed immunofluorescent image. The training data 215 can include input multiplexed immunofluorescent images and adjusted images based on the output. For example, the machine-learning model can learn to crop images predicted to include auto-fluorescent artifacts within a predefined distance (e.g., number of pixels) from a boundary of the multiplexed immunofluorescent image. The machine-learning model can additionally be trained to make other adjustments (e.g., filtering or removing auto-fluorescent artifacts) to the multiplexed immunofluorescent image.

In some instances, the training controller 210 determines or learns preprocessing parameters and/or approaches. For example, preprocessing can include filtering multiplexed immunofluorescent images based on features selected (e.g., to include multiplexed immunofluorescent images predicted to include auto-fluorescent artifacts, to exclude multiplexed immunofluorescent images predicted to not include auto-fluorescent artifacts). Preprocessing may include scanning an un-stained tissue slide (e.g., using a Mpx scanner). Auto-fluorescence in the unstained tissue slide can be determined and used to correct on a stained slide during subsequent processing. Other exemplary preprocessing can include normalizing or standardizing multiplexed immunofluorescent images.

A machine learning (ML) execution handler 240 can use the architecture and learned parameters to process non-training data and generate a result. For example, ML execution handler 240 may access a multiplexed immunofluorescent image of a slice of specimen not represented in the training data 215. The multiplexed immunofluorescent image may be stained with tyramide-based staining. In some instances, the multiplexed immunofluorescent image can be generated prior to the analysis system 205 accessing the multiplexed immunofluorescent image. The multiplexed immunofluorescent image can be captured subsequent to the stain being applied and can depict a sample stained with multiple stains corresponding to different biomarkers, which can facilitate (for example) determining a spatial relationship between different cell types (e.g., tumorous and non-tumorous cells). An image can be generated for each stain that is applied. The images for each stain can be combined to create the multiplexed immunofluorescent image. After an image is captured of the sample with a stain, the stain may be removed with a heat wash or chemical treatment between each imaging and stain application. As an example, a first stain for a first biomarker can be applied to a sample slice of the specimen. The first biomarker can be a protein indicative of a first type of tumor. A first image can be generated of the sample slice with the first stain. A second stain for a second biomarker can be applied to the sample slice of the specimen. The second biomarker can be a protein indicative of a second type of tumor. A second image can be generated of the sample slice with the second stain. The first image and second image can be combined to generate the multiplexed immunofluorescent image. The multiplexed immunofluorescent image may alternatively be generated after the multiple stains have been applied, such that there is no combining of images. In such examples, the stain may not be removed before the next stain is applied.

In some embodiments, the multiplexed immunofluorescent image generated or obtained is an RGB image or multispectral image. In some embodiments, the multiplexed immunofluorescent image generated is stored in a memory device. The multiplexed immunofluorescent image may be generated using the imaging device 235. In some embodiments, the image is generated or obtained from a microscope or other instrument capable of capturing image data of a specimen-bearing microscope slide, as described herein. In some embodiments, the multiplexed immunofluorescent image is generated or obtained using a 2D scanner, such as one capable of scanning image tiles. Alternatively, the multiplexed immunofluorescent image may have been previously generated (e.g. scanned) and stored in a memory device (or, for that matter, retrieved from a server via a communication network).

In some instances, the computing system 200 can receive a whole slide image prior to accessing the multiplexed immunofluorescent image. The whole slide image can include one or more patches. The patches may be a relatively small size (e.g., 256×256). A patch can be selected based on features (e.g., edges) being identified in the patch. The selected patch can correspond to the multiplexed immunofluorescent image and be processed with the trained machine-learning model. The computing system 200 may select one or more patches of the whole slide image that can then be processed using the machine-learning model.

In some instances, the multiplexed immunofluorescent image may (but need not) be preprocessed in accordance with a learned or identified preprocessing technique. For example, the ML execution handler 240 may unmix the multiplexed immunofluorescent image into its constituent channels before processing the image with the machine-learning model. Each unmixed channel can correspond to a particular stain or signal. In some embodiments, the unmixed images (often referred to as "channel images" or "image channel images") may be used as the input for the machine-learning model. The (preprocessed or original) multiplexed immunofluorescent image may be fed into a machine-learning model having an architecture (e.g., U-Net) used during training and configured with learned parameters. The architecture may involve an unmixing module to generate image channel images corresponding to one or more stain channels.

Figures 3A, 3B:
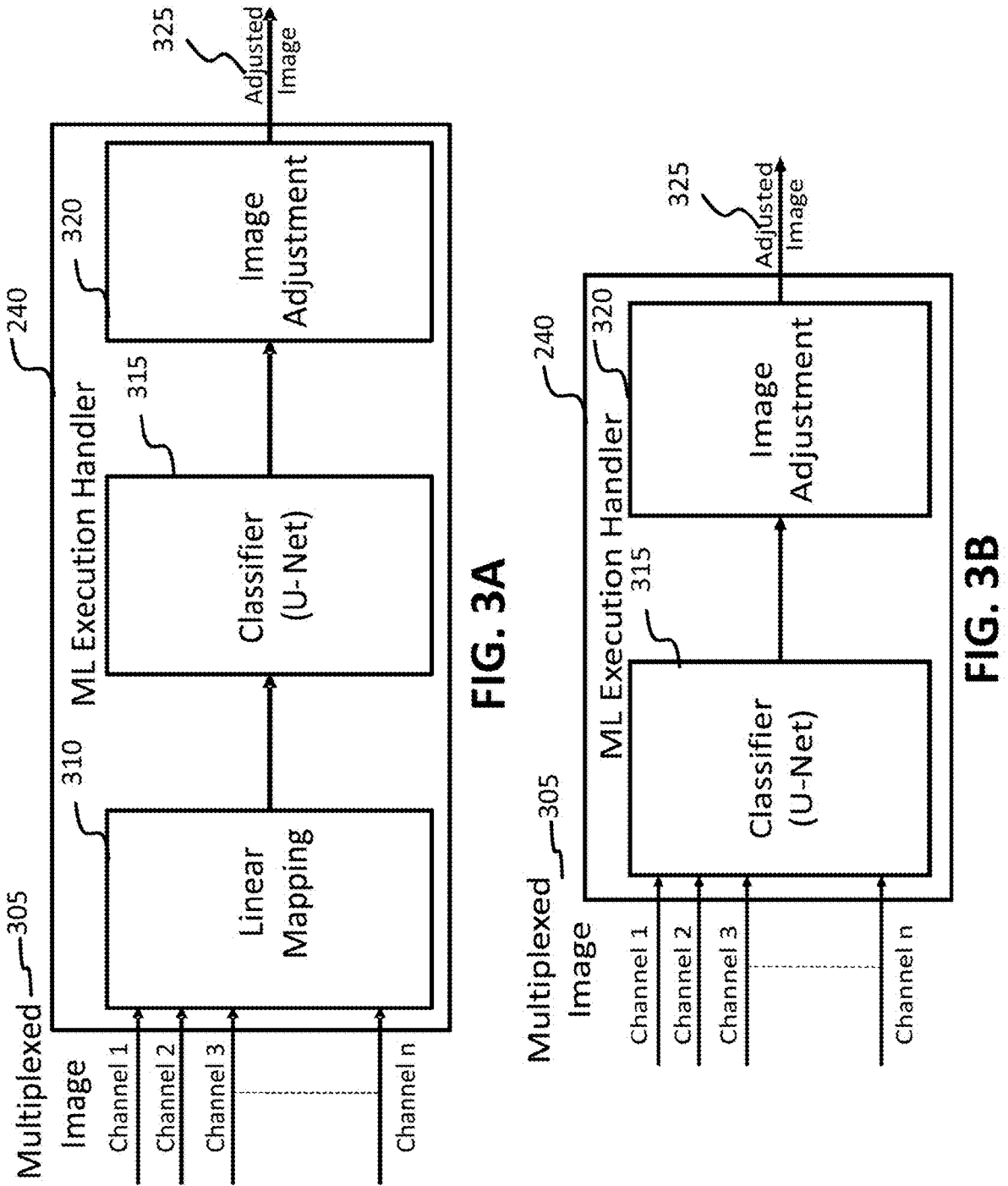
FIGS. 3A-3C show exemplary machine-learning model implementations for auto-fluorescent artifact prediction.
Figure 3C:
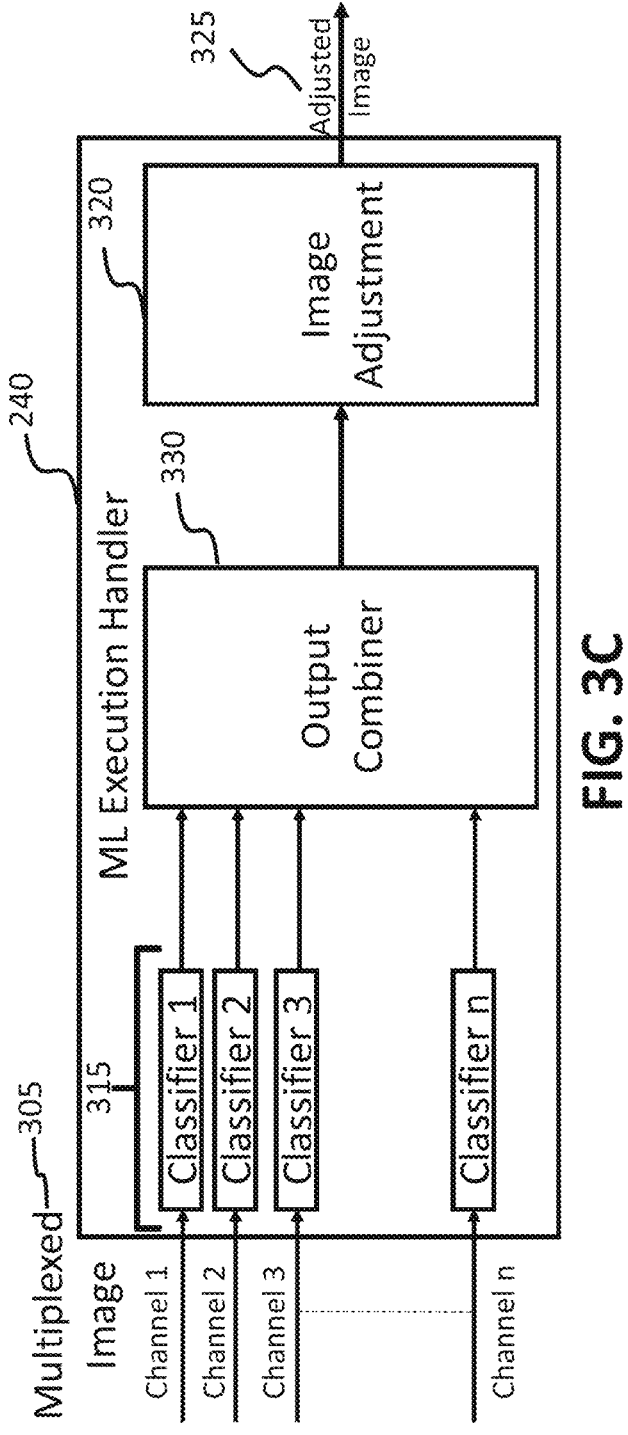

FIGS. 3A-3C show exemplary implementations for the ML execution handler 240. As shown in FIG. 3A, the ML execution handler 240 may receive multi-channel raw data (e.g., channel images) of the multiplexed immunofluorescent image 305. The ML execution handler 240 can perform linear mapping 310 to generate a composite image of the multiplexed immunofluorescent image 305. The linear mapping 310 can include combining features of each channel image to create the composite image. Alternatively, the ML execution handler 240 can perform nonlinear mapping or another suitable technique to generate the composite image of the multiplexed immunofluorescent image 305. The composite image can be input to the classifier 315. The classifier 315 may be a U-Net model or any other suitable model (e.g., V-Net, ResNet, etc.). The classifier 315 can be trained using labeled composite images. For example, the labeled composite images can include a first label for composite images including auto-fluorescent artifacts and a second label for composite images not including auto-fluorescent artifacts. The classifier 315 can output a prediction that the composite image includes one or more auto-fluorescent artifacts at one or more particular portions (e.g., a single pixel or multiple pixels) of the composite image. For example, the prediction may include a probability or likelihood that the composite image includes auto-fluorescent artifacts at certain areas of the composite image. In some examples, the ML execution handler 240 performs image adjustment 320 based on the prediction. For example, the ML execution handler 240 may crop or filter the composite image based on the prediction to generate an adjusted image 325. In other examples, the ML execution handler 240 can output the prediction without performing image adjustment 320.

In FIG. 3B, the ML execution handler 240 receives the multi-channel raw data of the multiplexed immunofluorescent image 305. The multi-channel raw data is used as input to the classifier 315. The classifier 315 can be trained using labeled multi-channel raw data of multiplexed immunofluorescent images. For example, the labeled multiplexed immunofluorescent images can include a first label for multiplexed immunofluorescent images including auto-fluorescent artifacts and a second label for multiplexed immunofluorescent images not including auto-fluorescent artifacts. The classifier 315 can output a prediction that the multiplexed immunofluorescent image 305 includes one or more auto-fluorescent artifacts at one or more particular portions of the multiplexed immunofluorescent image. In some examples, the ML execution handler 240 performs image adjustment 320 on the multiplexed immunofluorescent image 305 based on the prediction to generate the adjusted image 325 for subsequent processing. In other examples, the ML execution handler 240 can output the prediction without performing image adjustment 320.

As shown in FIG. 3C, the ML execution handler 240 can process and classify each channel image of the multi-channel raw data of the multiplexed immunofluorescent image 305 with a corresponding classifier 315. Each classifier 315 can be trained for a different channel (e.g., stain or signal). Each classifier 315 can output a prediction that the corresponding channel image includes one or more auto-fluorescent artifacts at one or more portions of the corresponding channel image. An output combiner 330 of the ML execution handler 240 may then combine the predictions of each channel image. For example, the output combiner 330 can average the prediction for each corresponding pixel in each channel image to determine a combined prediction for the multiplexed immunofluorescent image 305. The combined prediction may provide increased accuracy of auto-fluorescent artifact prediction since the combined prediction takes into account multiple predictions for each pixel. In some examples, the ML execution handler 240 performs image adjustment 320 on the multiplexed immunofluorescent image 305 based on the combined prediction to generate the adjusted image 325 for subsequent processing. In other examples, the ML execution handler 240 can output the combined prediction without performing image adjustment 320.

Returning to FIG. 2, in some instances, subsequent image processing is performed by an image processor 245. The subsequent image processing can be adjusted based on the prediction that the multiplexed immunofluorescent image includes auto-fluorescent artifacts. For example, adjusting the subsequent image processing can include determining that at least one metric corresponding to the particular portions (e.g., one or more pixels) of the multiplexed immunofluorescent image exceeds a predefined threshold. The determination may be performed for each of one or more regions of the multiplexed immunofluorescent image. Examples of the metric can include a cumulative size of the auto-fluorescent artifacts (e.g., a number of pixels depicting at least part of an artifact), a number of auto-fluorescent artifacts, a mean intensity of auto-fluorescent artifacts, and/or probability that the multiplexed immunofluorescent image includes at least one auto-fluorescent artifacts. For example, a predefined threshold for the probability that a particular portion includes auto-fluorescent artifacts may be 70%. Based on determining a particular portion of the multiplexed immunofluorescent image has a probability of including auto-fluorescent artifacts above 70%, the subsequent image processing can be adjusted.

In some instances, the image processor 245 may generate a modified version of the multiplexed immunofluorescent image based on the prediction. Generating the modified version may include applying filters or other image-enhancing techniques to each of the predicted particular portions of the multiplexed immunofluorescent image containing auto-fluorescent artifacts. The modified version of the multiplexed immunofluorescent image can then be processed with the machine-learning model.

In some instances, the subsequent image processing includes modifying one or more other images based on locations of the particular portions predicted to include auto-fluorescent artifacts in the multiplexed immunofluorescent image. The other images can correspond to another slice of the specimen. Modifying the other images may include filtering or segmenting the other images at locations in the other slice of the specimen that correspond to the locations of the particular portions in the multiplexed immunofluorescent image. The other images can then be processed with one or more machine-learning models to determine a predicted characterization of the specimen.

In some instances, an image characterizer 250 identifies a predicted characterization for the multiplexed immunofluorescent image based on the execution of the subsequent image processing. The execution may itself produce a result that includes the characterization, or the execution may include results that image characterizer 250 can use to determine a predicted characterization of the specimen. For example, the subsequent image processing may include detecting depictions of a set of tumor cells. A result may characterize a presence, quantity of, and/or size of the set of tumor cells. Image characterizer 250 may apply rules and/or transformations to map the probability and/or confidence to a characterization. As an illustration, a first characterization may be assigned if a result includes a probability greater than 50% that the multiplexed immunofluorescent image includes a set of tumor cells, and a second characterization may be otherwise assigned.

A communication interface 255 can collect results and communicate the result(s) (or a processed version thereof) to a user device (e.g., associated with a laboratory technician or care provider) or other system. For example, communication interface 255 may generate an output that identifies the presence of, quantity of and/or size of the set of tumor cells. The output may then be presented and/or transmitted, which may facilitate a display of the output data, for example on a display of a computing device.

IV. Exemplary U-Net Model

Figure 4:
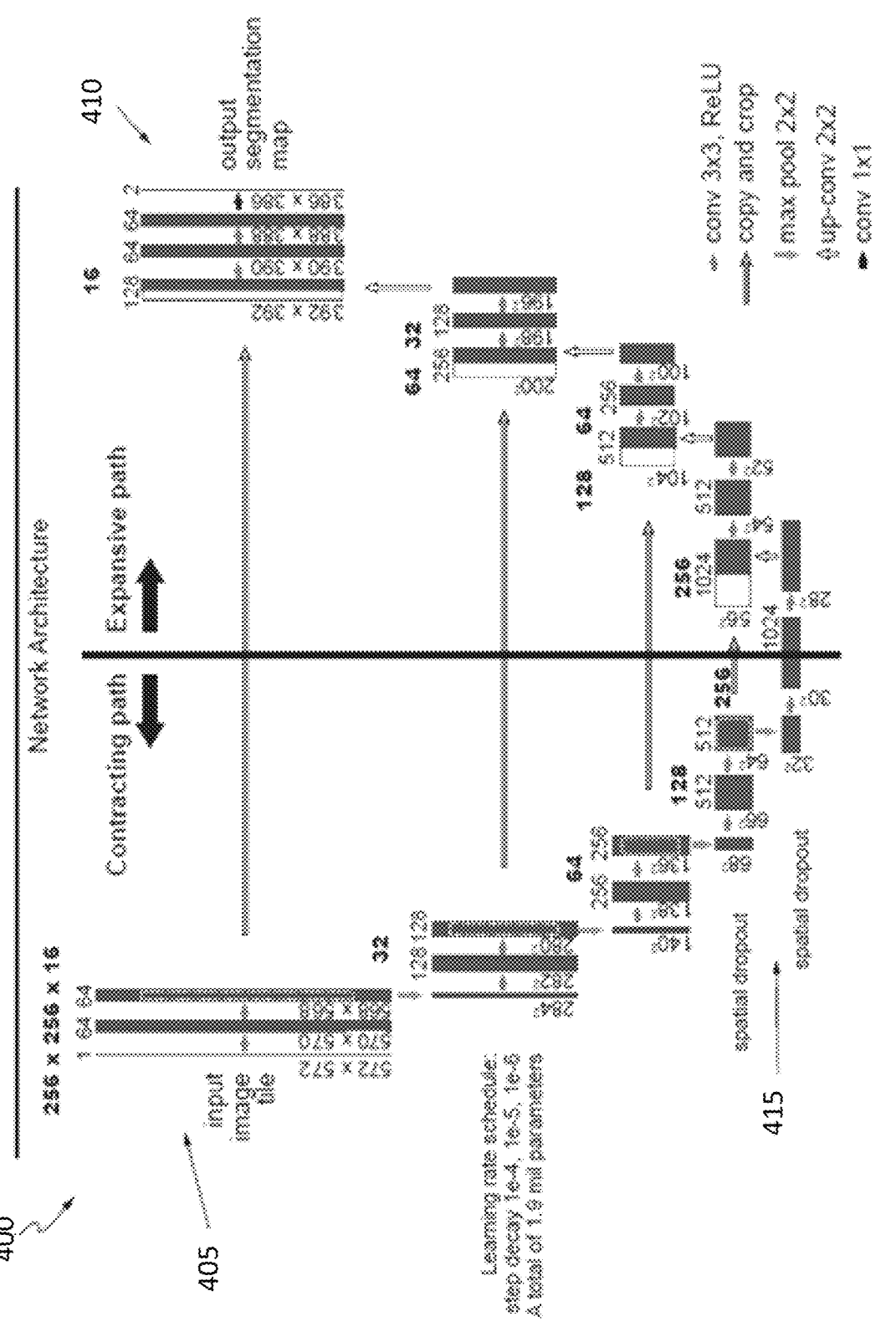
FIG. 4 shows an exemplary U-Net according to various embodiments.

As shown in FIG. 4, a U-Net 400 may include a contracting path 405 (encoder) and an expansive path 410 (decoder), which gives it a u-shaped architecture. The contracting path 405 is a CNN network that includes repeated application of convolutions (e.g., 3×3 convolutions (unpadded convolutions)), each followed by a rectified linear unit (ReLU) and a max pooling operation (e.g., a 2×2 max pooling with stride 2) for downsampling. At each downsampling step or pooling operation, the number of feature channels may be doubled. During the contraction, the spatial information of the image data is reduced while feature information is increased. The expansive path 410 is a CNN network that combines the feature and spatial information from the contracting path 405 (upsampling of the feature map from the contracting path 405). The upsampling of the feature map is followed by a sequence of up-convolutions (upsampling operators) that halves the number of channels, concatenations with a correspondingly cropped feature map from the contracting path 405, repeated application of convolutions (e.g., two 3×3 convolutions) that are each followed by a rectified linear unit (ReLU), and a final convolution (e.g., one 1×1 convolution) to generate the two-dimensional non-target region masks. In order to localize, the high-resolution features from the contracting path 405 are combined with the upsampled output from the expansive path 410.

In various embodiments, the U-Net 400 implements a number of channels that is reduced overall from that of a conventional U-Net architecture. Specifically, the number of channels of the intermediate activation output layers is reduced by a predetermined factor such as two or four (see e.g., the bold numbers within the contracting path 405 and the expansive path 410), for example, in the second layer, the number of channels is reduced by a factor of four from 64 to 16, etc., and the max number of channels is also reduced by a factor of four to 256 instead of 1024 as used in a conventional U-Net architecture. This reduction in channels is implemented to reduce the computation expense and model complexity. This compressed U-Net architecture may provide better results as compared to a conventional U-Net architecture having a max number of 1024 channels and no reduction in the number of channels. Moreover, the U-Net 400 comprises a spatial drop out 415 to combat overfitting. The spatial drop out 415 may be implemented in the last few layers (i.e., the last one, two, three, or four layers) of the contracting path 405. The spatial drop out 415 drops entire two-dimensional feature maps instead of individual elements as performed by conventional drop out. For example, if adjacent pixels within feature maps are strongly correlated (as is normally the case in early convolution layers) then conventional dropout will not regularize the activations and will otherwise result in an effective learning rate decrease. In contrast, the spatial drop out 415 will regularize the activations and help promote independence between feature maps and will otherwise result in an effective learning rate increase.

V. Example Model Results

FIGS. 5-8 show exemplary training accuracy results generated from four experiments using a trained machine-learning model (e.g., U-Net model). Specifically, the results correspond to data elements accessed from a database of patches of multiplexed immunofluorescent images. For FIGS. 5-7, the data was divided into classes and test and training datasets as described with respect to FIG. 2. The data was split into 80% for training and 20% for testing. In this exemplary instance, a binary cross entropy loss function was used to train the modified U-Net using 50 epochs, a batch size of 2, and a learning rate of $1\times10^{-5}$.

Figure 5:
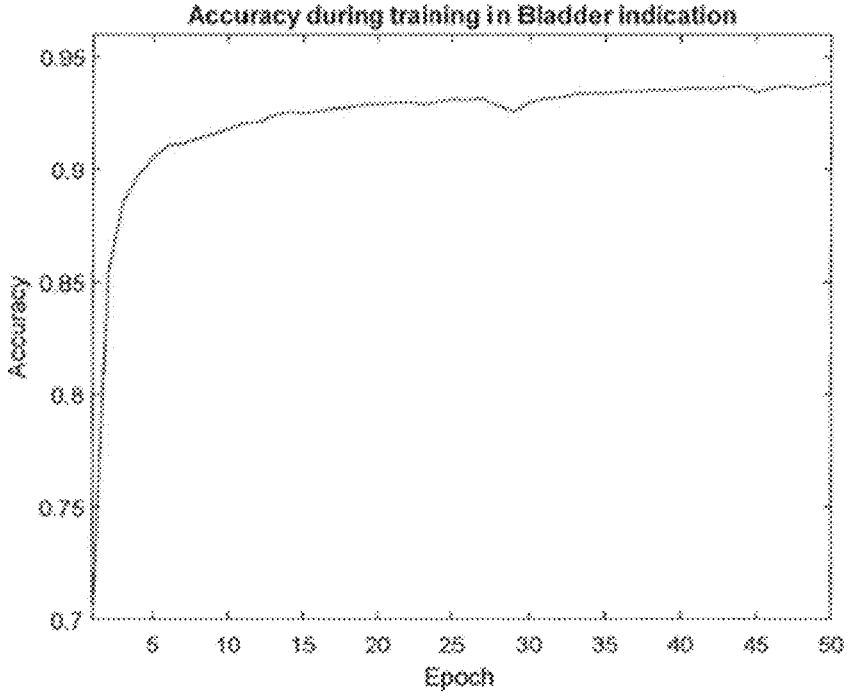
FIG. 5 shows exemplary training accuracy results generated using a trained machine-learning model for a single tissue indication.
Figure 5:
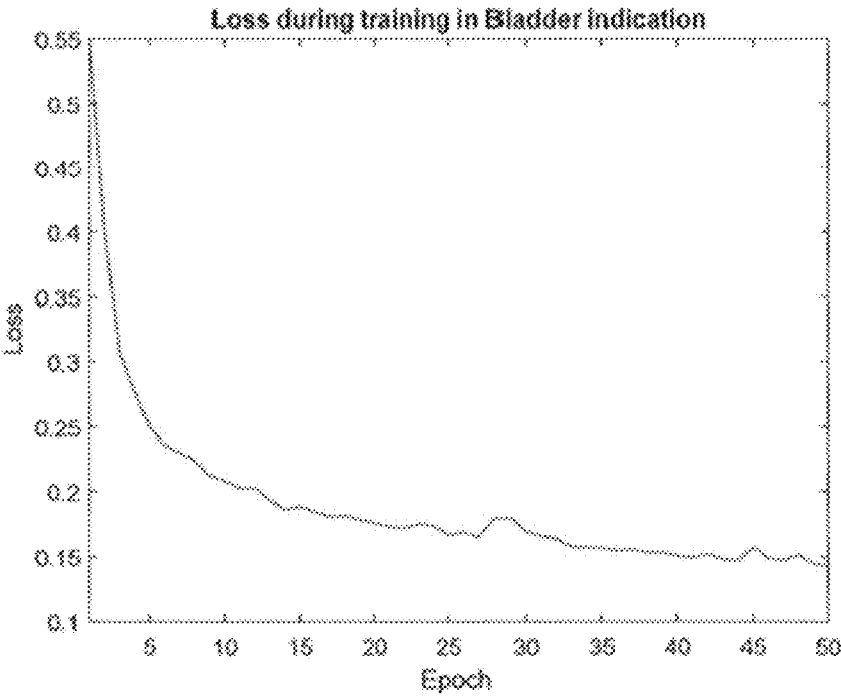

FIG. 5 shows exemplary results for using the trained machine-learning model for a single tissue indication (e.g., bladder). For this experiment, 152 patches were used to train and test the machine-learning model. The accuracy and loss during training are shown. The accuracy increased across epochs as the loss decreased. The training accuracy was 93.9% and the training losses were 0.142, while the accuracy for the test data was 85.6% and the losses for the test data were 0.149.

Figure 6:
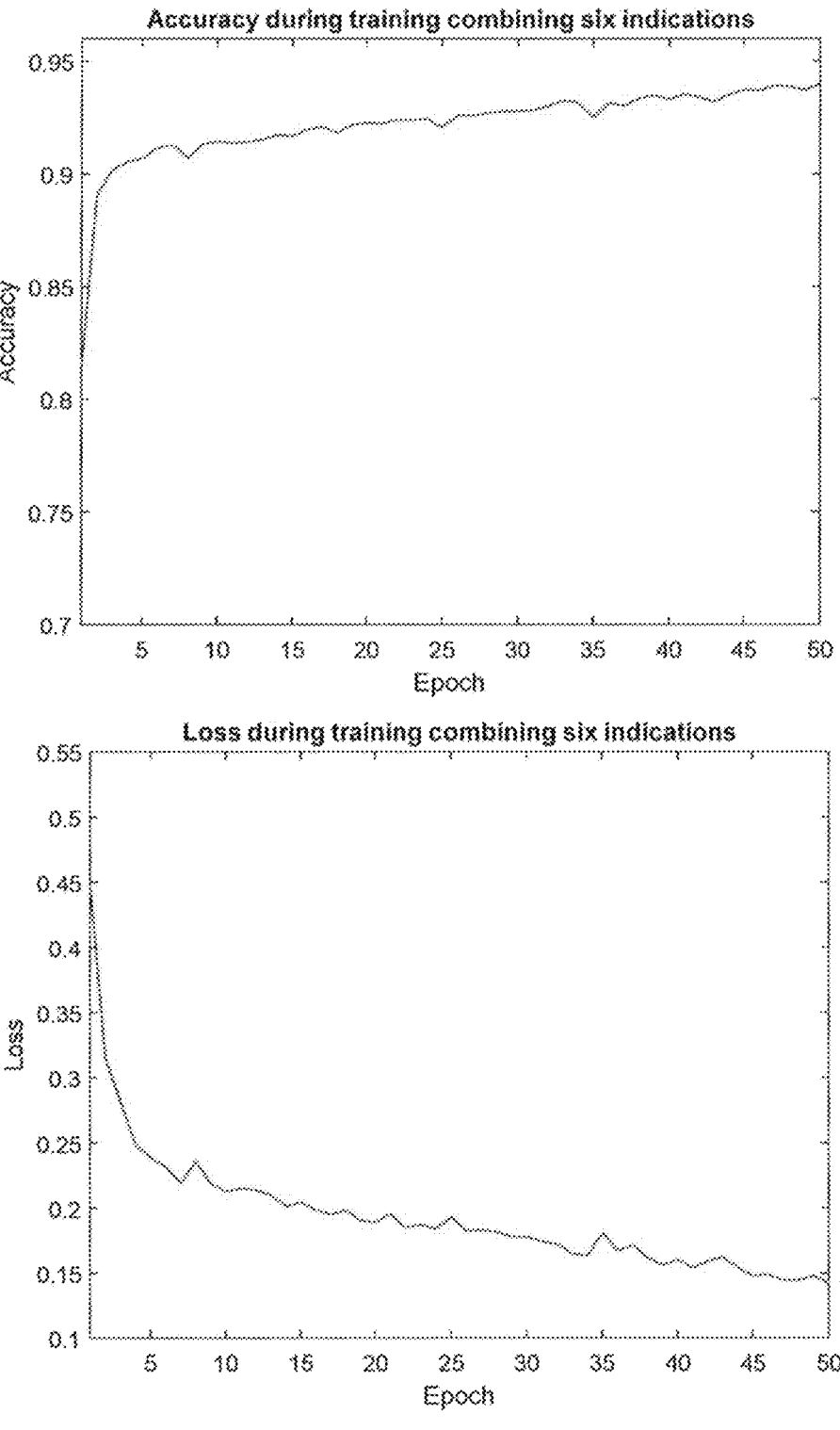
FIG. 6 shows exemplary training accuracy results generated using a trained machine-learning model for six tissue indications.

FIG. 6 shows exemplary results using the trained machine-learning model for six tissue indications. The tissue indications include colorectal cancer, lung, breast, pancreas, gastric, and bladder. For this experiment, 275 patches were accessed from the database. The accuracy and loss during training are shown, with the accuracy increasing across epochs as the loss decreases. The results for this experiment improved from the single tissue indication experiment, with a training accuracy of 95.2% and training losses of 0.113. Additionally, accuracy for the test data was 85.6% and the losses for the test data were 0.148.

Figure 7:
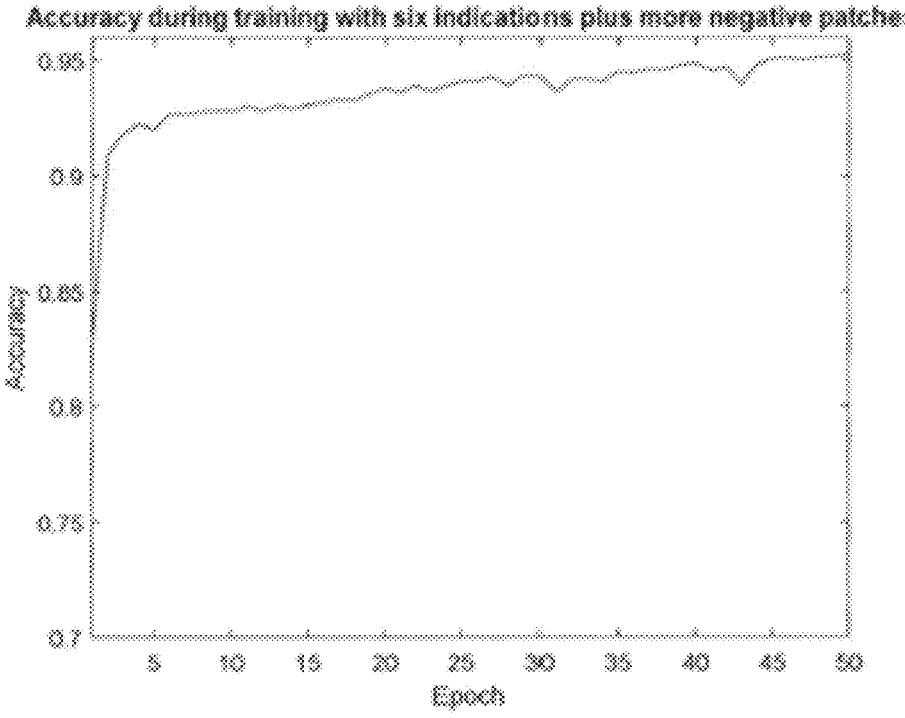
FIG. 7 shows exemplary training accuracy results generated using a trained machine-learning model for patches with six tissue indications and negative patches.
Figure 7:
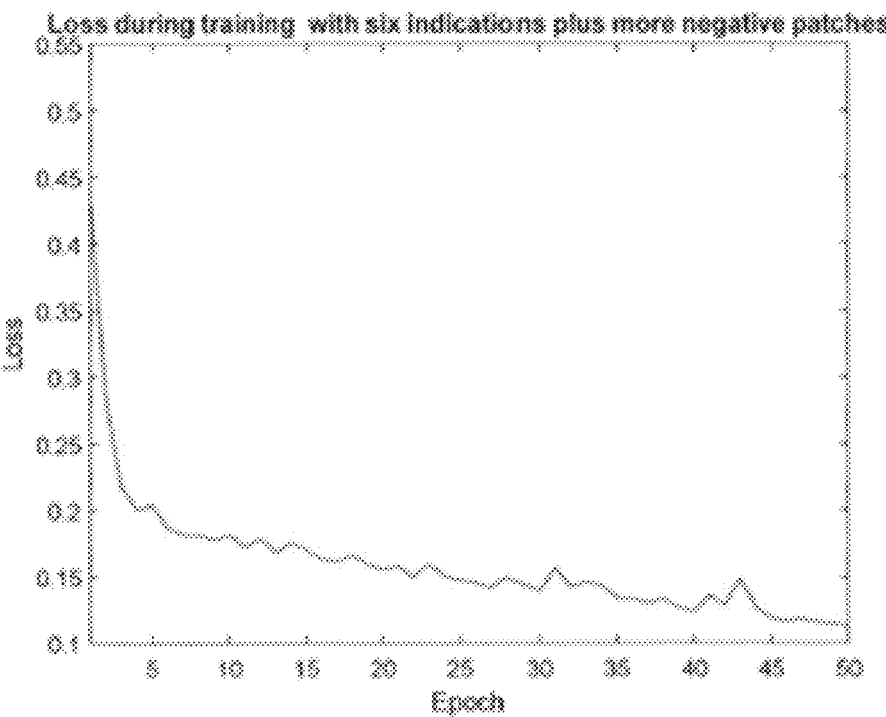

FIG. 7 shows exemplary results using the trained machine-learning model for patches with six indications (e.g., colorectal cancer, bladder, breast, pancreas, lung, gastric) and negative patches. The negative patches correspond to patches with no auto-fluorescent artifacts present. For this experiment, 344 patches were accessed from the database. The accuracy and loss during the modified U-Net training with respect to the epochs is shown. The accuracy increased across epochs as the loss decreased. The training accuracy was 95.2% and the training losses were 0.113. In this experiment, the accuracy for the test data was the highest at 88.3%. Additionally, the losses for the test data were lowest at 0.119.

Figure 8:
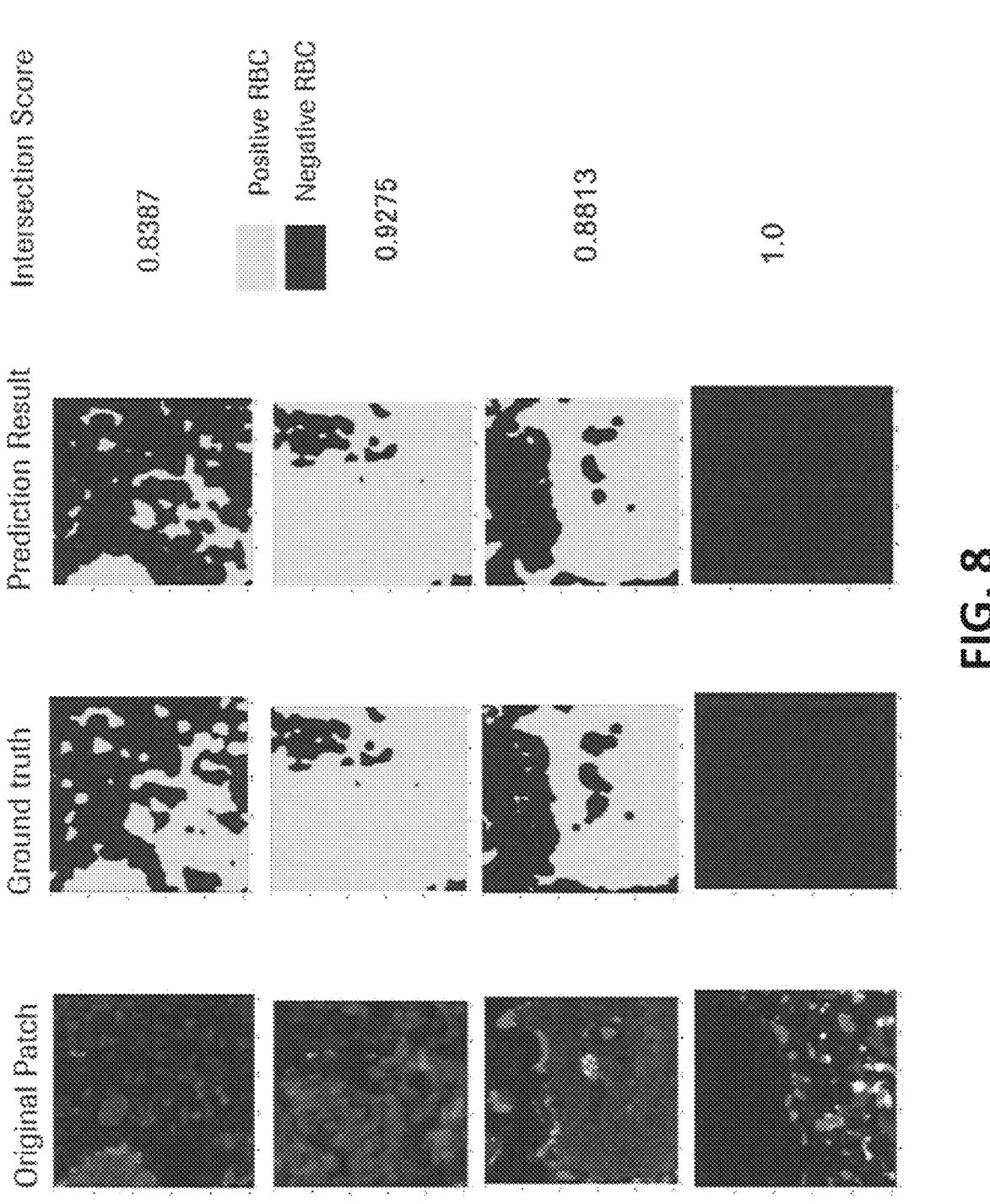
FIG. 8 shows exemplary results of comparing predictions of a trained machine-learning model with known ground truths.

FIG. 8 shows exemplary results of comparing predictions of the trained machine-learning model with known ground truths (e.g., pixels known to include or not to include auto-fluorescent artifacts). Four patches were tested from the database. A pixel-to-pixel agreement between the machine-learning model predictions and the ground truths was calculated for each patch. For red blood cell prediction, the prediction from the machine-learning model agreed with the ground truths for between 84%-100% of the pixels.

VI. Example Use Cases

Figure 9:
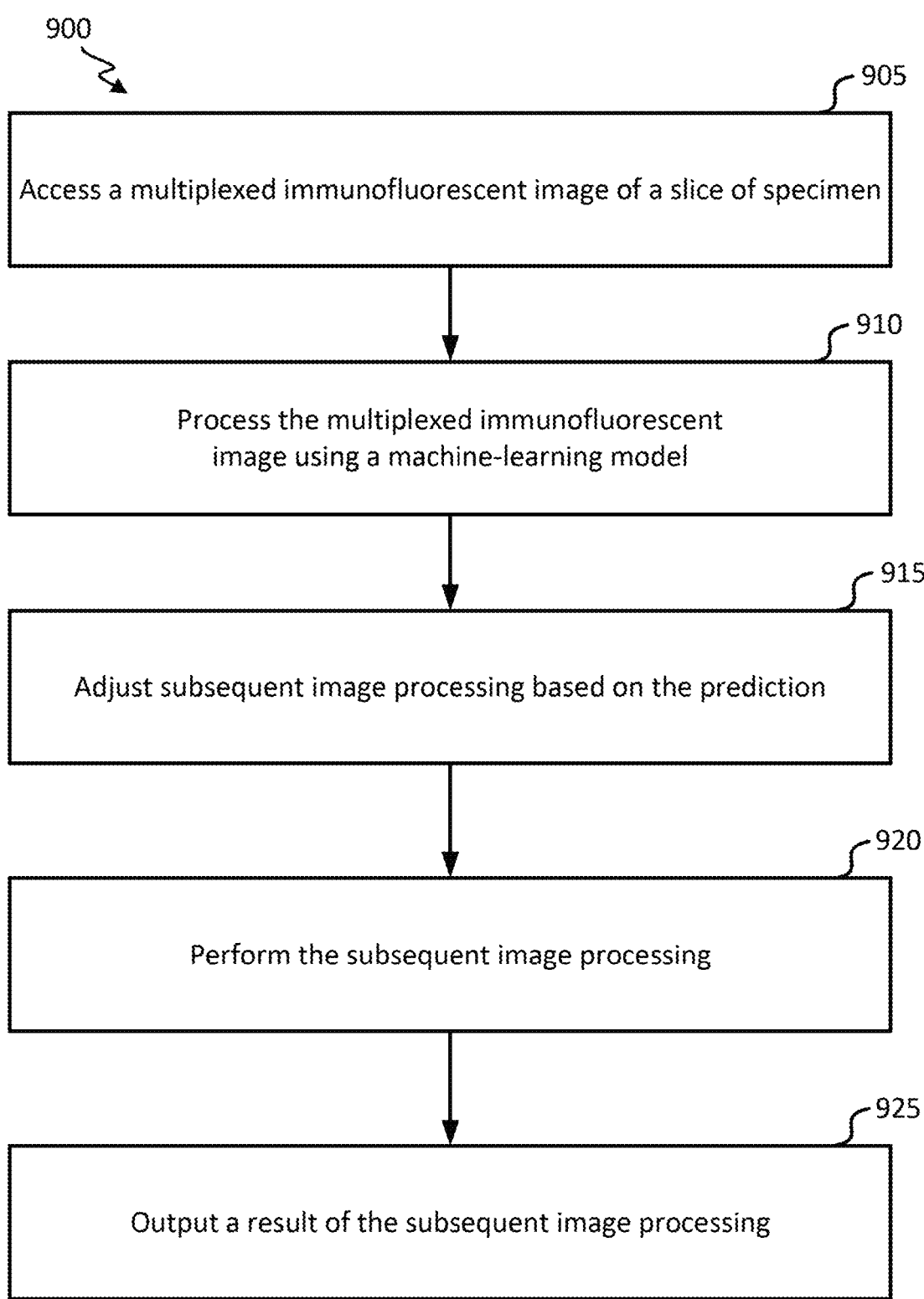
FIG. 9 illustrates an exemplary process of using a machine-learning model to identify auto-fluorescent artifacts.

FIG. 9 illustrates a process 900 of using a machine-learning model to identify auto-fluorescent artifacts in a multiplexed immunofluorescent image. At block 905, a multiplexed immunofluorescent image of a slice of specimen is accessed. The multiplexed immunofluorescent image may correspond to a whole slide image or a patch of a whole slide image with auto-fluorescent artifacts. The multiplexed immunofluorescent image can be stained with multiple stains for determining a characterization of a set of tumor cells. Pre-processing may be performed on the multiplexed immunofluorescent image for feature selection.

At block 910, a machine-learning model processes the multiplexed immunofluorescent image. The machine-learning model can be trained with training multiplexed immunofluorescent images that include some images with auto-fluorescent artifacts and some images without auto-fluorescent artifacts. The machine-learning model can be a deep neural network and/or a convolutional neural network. The machine-learning model can include a U-Net model. An output of the machine-learning model can be a prediction of particular portions (e.g., one or more pixels) of the multiplexed immunofluorescent image that depict auto-fluorescent artifacts.

At block 915, subsequent image processing is adjusted based on the prediction. The adjustments can include generating a modified version of the multiplexed immunofluorescent image. Other images corresponding to another slice of the specimen may also be modified. The other images may be modified based on locations of the particular portions predicted to include auto-fluorescent artifacts. Additionally, adjusted subsequent image processing can involve determining a metric (e.g., a cumulative size of auto-fluorescent artifacts, a probability of including an auto-fluorescent artifact, a mean intensity of auto-fluorescent artifacts) corresponding to the particular portions of the multiplexed immunofluorescent image exceeds a predefined threshold. The determination can be for each of one or more regions of the multiplexed immunofluorescent image. The metric can include at least part of the output of the processing. Alternatively, the metric may be generated based on the output of the processing.

At block 920, the subsequent image processing is performed. One or more trained machine learning models or other image analysis techniques may be used for the subsequent image processing. The subsequent image processing can include processing the modified version of the multiplexed immunofluorescent image. The subsequent image processing can also include processing the one or more other images that were modified based on the prediction of the machine-learning model. In some instances, the subsequent image processing can include detecting depictions of a set of tumor cells.

At block 925, a result of the subsequent image processing is output. For example, the result may be transmitted to another device (e.g., associated with a care provider) and/or displayed. The result can correspond to a predicted characterization of the specimen. The result can characterize a presence of, quantity of, and/or size of the set of tumor cells. The result may characterize more than one set of tumor cells for the multiplexed immunofluorescent image. For example, each stain of the multiplexed immunofluorescent image can correspond to a different set of tumor cells and the result can characterize each set of tumor cells. The result may be used for diagnosis or treatment assessment of a subject.

FIG. 9 shows one exemplary process for using a machine-learning model to identify auto-fluorescent artifacts in a multiplexed immunofluorescent image. Other examples can include more steps, fewer steps, different steps, or a different order of steps. For example, auto-fluorescent artifact identification can occur after tumor detection and classification as post-processing steps to exclude the identified auto-fluorescent artifacts.

VII. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

The description herein provides preferred exemplary embodiments only, and is not intended to limit the scope, applicability or configuration of the disclosure. Rather, the description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the description herein to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A computer-implemented method comprising:
accessing a multiplexed immunofluorescent image of a slice of specimen, wherein the multiplexed immunofluorescent image comprises one or more auto-fluorescent artifacts;
processing the multiplexed immunofluorescent image using a machine-learning model, wherein an output of the processing corresponds to a prediction that the multiplexed immunofluorescent image includes one or more auto-fluorescent artifacts at one or more particular portions of the multiplexed immunofluorescent image;
adjusting subsequent image processing based on the prediction;
performing the subsequent image processing; and
outputting a result of the subsequent image processing, wherein the result corresponds to a predicted characterization of the specimen.

2. The computer-implemented method of claim 1, further comprising:
generating a modified version of the multiplexed immunofluorescent image based on the prediction of each of the one or more auto-fluorescent artifacts, wherein the subsequent image processing includes processing the modified version of the multiplexed immunofluorescent image.

3. The computer-implemented method of claim 1, wherein adjusting the subsequent image processing includes:
determining, for each of one or more regions of the multiplexed immunofluorescent image, that at least one metric corresponding to the one or more particular portions of the multiplexed immunofluorescent image exceeds a predefined threshold, wherein the at least one metric includes at least part of or is generated based on the output of the processing.

4. The computer-implemented method of claim 1, wherein performing the subsequent image processing includes:
modifying each of one or more other images based on locations of the one or more particular portions of the multiplexed immunofluorescent image, each of the one or more other images corresponding to another slice of the specimen; and
processing the modified one or more other images.

5. The computer-implemented method of claim 1, wherein the one or more auto fluorescent artifacts depict one or more red blood cells.

6. The computer-implemented method of claim 1, wherein the machine-learning model comprises a U-Net model.

7. The computer-implemented method of claim 1, further comprising:
receiving, prior to accessing the multiplexed immunofluorescent image, a whole slide image comprising one or more patches; and
selecting a patch of the one or more patches based on identifying features in the patch, wherein the patch corresponds to the multiplexed immunofluorescent image.

8. The computer-implemented method of claim 1, further comprising, prior to accessing the multiplexed immunofluorescent image:
applying a first stain for a first biomarker to a sample slice of the specimen;
generating a first image of the sample slice with the first stain;
applying a second stain for a second biomarker to the sample slice of the specimen;

generating a second image of the sample slice with the second stain; and combining the first image and the second image to generate the multiplexed immunofluorescent image.

9. The computer-implemented method of claim 1, wherein performing the subsequent image processing includes detecting depictions of a set of tumor cells, and wherein the result characterizes a presence of, quantity of and/or size of the set of tumor cells.

10. The computer-implemented method of claim 1, wherein the multiplexed immunofluorescent image includes tyramide-based staining for the slice of specimen.

11. The computer-implemented method of claim 1, wherein processing the multiplexed immunofluorescent image using the machine-learning model comprises:

receiving channel images of the multiplexed immunofluorescent image;

combining the channel images to generate a composite image; and processing the composite image using the machine-learning model.

12. The computer-implemented method of claim 1, wherein the machine-learning model is a first machine-learning model and processing the multiplexed immunofluorescent image using the machine-learning model comprises:

receiving channel images of the multiplexed immunofluorescent image;

processing a first channel image of the channel images using the first machine-learning model; and processing additional channel images of the channel images using additional corresponding machine-learning models.

13. The computer-implemented method of claim 1, wherein processing the multiplexed immunofluorescent image using the machine-learning model further comprises:

adjusting the multiplexed immunofluorescent image based on the prediction to generate an adjusted image; and outputting the adjusted image for subsequent image processing.

14. A system comprising:

one or more data processors; and a non-transitory computer readable storage medium containing instructions which, when executed on the one or more data processors, cause the one or more data processors to perform operations comprising:

accessing a multiplexed immunofluorescent image of a slice of specimen, wherein the multiplexed immunofluorescent image comprises one or more auto fluorescent artifacts;

processing the multiplexed immunofluorescent image using a machine-learning model, wherein an output of the processing corresponds to a prediction that the multiplexed immunofluorescent image includes one or more auto-fluorescent artifacts at one or more particular portions of the multiplexed immunofluorescent image;

adjusting subsequent image processing based on the prediction;

performing the subsequent image processing; and outputting a result of the subsequent image processing, wherein the result corresponds to a predicted characterization of the specimen.

15. The system of claim 14, wherein the non-transitory computer readable medium further contains instructions which, when executed on the one or more data processors, cause the one or more data processors to perform operations comprising:

generating a modified version of the multiplexed immunofluorescent image based on the prediction of each of the one or more auto-fluorescent artifacts, wherein the subsequent image processing includes processing the modified version of the multiplexed immunofluorescent image.

16. The system of claim 14, wherein adjusting the subsequent image processing includes:

determining, for each of one or more regions of the multiplexed immunofluorescent image, that at least one metric corresponding to the one or more particular portions of the multiplexed immunofluorescent image exceeds a predefined threshold, wherein the at least one metric includes at least part of or is generated based on the output of the processing.

17. The system of claim 14, wherein performing the subsequent image processing comprises:

modifying each of one or more other images based on locations of the one or more particular portions of the multiplexed immunofluorescent image, each of the one or more other images corresponding to another slice of the specimen; and processing the modified one or more other images.

18. The system of claim 14, wherein the one or more auto-fluorescent artifacts depict one or more red blood cells.

19. The system of claim 14, wherein the machine-learning model comprises a U Net model.

20. A computer-program product tangibly embodied in a non-transitory machine-readable storage medium, including instructions configured to cause one or more data processors to perform operations comprising:

accessing a multiplexed immunofluorescent image of a slice of specimen, wherein the multiplexed immunofluorescent image comprises one or more auto-fluorescent artifacts;

processing the multiplexed immunofluorescent image using a machine-learning model, wherein an output of the processing corresponds to a prediction that the multiplexed immunofluorescent image includes one or more auto-fluorescent artifacts at one or more particular portions of the multiplexed immunofluorescent image; and adjusting subsequent image processing based on the prediction;

performing the subsequent image processing; and outputting a result of the subsequent image processing, wherein the result corresponds to a predicted characterization of the specimen.

* * * * *